United States Patent
Yuan et al.

(10) Patent No.: US 11,717,702 B2
(45) Date of Patent: Aug. 8, 2023

(54) 3D DEEP PLANNING RADIOTHERAPY SYSTEM AND METHOD

(71) Applicant: Icahn School of Medicine at Mount Sinai, New York, NY (US)

(72) Inventors: Yading Yuan, New York, NY (US); Tzu-Chi Tseng, New York, NY (US); Yeh-Chi Lo, New York, NY (US)

(73) Assignee: ICAHN School of Medicine at Mount Sinai, New York, NY (US)

( * ) Notice: Subject to any disclaimer, the term of this patent is extended or adjusted under 35 U.S.C. 154(b) by 599 days.

(21) Appl. No.: 16/633,567

(22) PCT Filed: Jul. 30, 2018

(86) PCT No.: PCT/US2018/044424
§ 371 (c)(1),
(2) Date: Jan. 23, 2020

(87) PCT Pub. No.: WO2019/027924
PCT Pub. Date: Feb. 7, 2019

(65) Prior Publication Data
US 2020/0155868 A1    May 21, 2020

Related U.S. Application Data

(60) Provisional application No. 62/538,763, filed on Jul. 30, 2017.

(51) Int. Cl.
*G16H 20/40* (2018.01)
*A61N 5/10* (2006.01)
*G16H 30/20* (2018.01)
*G06N 3/08* (2023.01)

(52) U.S. Cl.
CPC ............ *A61N 5/1031* (2013.01); *G06N 3/08* (2013.01); *G16H 20/40* (2018.01); *G16H 30/20* (2018.01)

(58) Field of Classification Search
CPC ........ A61N 5/1031; G06N 3/08; G16H 20/40; G16H 30/20
See application file for complete search history.

(56) References Cited

U.S. PATENT DOCUMENTS

2012/0014507 A1* 1/2012 Wu .......................... A61N 5/10
378/65
2015/0095044 A1* 4/2015 Hartman ................ A61N 5/103
705/2
2015/0124930 A1* 5/2015 Verhaegen ........... A61N 5/1047
250/252.1

(Continued)

FOREIGN PATENT DOCUMENTS

CN        106600571       4/2017
WO    WO 2014/205128    12/2014
WO    WO 2017/106645     6/2017

OTHER PUBLICATIONS

"International Search Report and Written Opinion in PCT application No. PCT/US2018/044424", dated Nov. 12, 2018, 8 pages.

*Primary Examiner* — Jason S Tiedeman
*Assistant Examiner* — Liza Tony Kanaan
(74) *Attorney, Agent, or Firm* — IP Spring

(57) ABSTRACT

Systems and methods for three-dimensional dose prediction and treatment planning using a deep learning fully convolutional neural network are disclosed.

20 Claims, 8 Drawing Sheets

(56) References Cited

U.S. PATENT DOCUMENTS

2015/0227702 A1\* 8/2015 Krishna ............... A61B 5/7257
                                                         705/2
2017/0177812 A1\* 6/2017 Sjölund ................ G16H 20/40
2019/0030370 A1\* 1/2019 Hibbard ............... A61N 5/1067

\* cited by examiner

3D DEEP PLANNING RADIOTHERAPY SYSTEM AND METHOD

CROSS-REFERENCE TO RELATED APPLICATIONS

This application is a U.S. national stage filing under 35 U.S.C. § 371 of International Application No. PCT/US18/44424, filed Jul. 30, 2018, which claims priority to U.S. Provisional Patent Application No. 62/538,763, filed Jul. 30, 2017, entitled, "3D DEEP PLANNING RADIOTHERAPY SYSTEM AND METHOD", and which is incorporated by reference herein in its entirety.

BACKGROUND

Cancer is thought to be the second leading cause of death worldwide after cardiovascular disease. A study from the American Cancer Society published in 2016 stated that every second male and every third female in the U.S. will be diagnosed with cancer during their lifetime. Radiotherapy, or radiation therapy, is one of three common forms of cancer treatment. Approximately 50% of cancer patients receive radiation therapy during the course of their illness.

Traditional workflows for designing radiotherapy treatment plans are often subjective and time-consuming with multiple manual interactions that may require several hours to several days to plan treatment for a patient. Further, treatment plans developed for a radiotherapy patient may provide a highly variable quality of treatment. Accordingly, the full potential of radiotherapy treatment may not be consistently achieved and patient care may be compromised.

Some implementations were conceived in light of the above-mentioned problems and limitations.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Some implementations are generally related to radiotherapy, and in particular to three-dimensional (3D) radiotherapy dose distribution prediction and treatment planning using deep learning systems and methods.

Some implementations can include a computer-implemented method to predict a three-dimensional (3D) dose distribution. For example, dose refers to parameters for radiation treatment, e.g., an amount of radiation to be applied in terms of units of radiation per unit of volume or mass, a time duration for which radiation is to be applied, a count of times radiation is to be applied, a type of radiation to be applied, a physical location within an organ of a patient, etc. For example, in the context of external beam radiation therapy, i.e., treating patients with LINAC, the output of the FCNN can include the predicted dose distribution in units of Gy, which is defined as energy deposited per unit of mass (Joule/kilogram). The output of the FCNN can be provided as input to subsequent stage (e.g., 3D inverse planning) to generate a clinically-deliverable plan, which can be done, for example, with a commercial treatment planning system. There are numerous parameters stored in a treatment plan. For example, in addition to those mentioned above, there are parameters associated with mechanical movements of some components in the LINAC, for example, the gantry rotation and the movements of multi-leaf collimators (MLCs), etc. These parameters can be generated by the commercial treatment planning systems with the input from the deep planning system. The method can include receiving input data including a three-dimensional voxel image, and providing at least a portion of the input data to a fully convolutional neural network (FCNN).

The method can also include programmatically analyzing the input data using the FCNN to generate a three-dimensional dose distribution prediction, and providing the three-dimensional dose distribution prediction as output.

The method can further include programmatically analyzing the three-dimensional dose distribution prediction to generate a treatment plan, wherein the treatment plan includes an electronic file that is operable to cause a radiotherapy system to treat the body of a patient using radiation, and transmitting the treatment plan to the radiotherapy system. In some implementations, the electronic file can include a data format accepted by a LINAC, such as an extension of DICOM, or Digital Imaging and Communications in Medicine, which is a standard for storing and transmitting medical images. The extension for radiation oncology can include DICOM-RT, in which RT stands for radiation therapy. Further, within DICOM, and a plurality of DICOM-RT objects, namely RT image, RT structure sets, RT plan, RT dose, RT beams treatment record, RT brachy treatment record, and RT treatment summary, have been created. In some implementations, the treatment plan can be an electronic file in the DICOM-RT format.

Some implementations can include a system having a hardware processor configured to perform the method mentioned above. In some implementations, the hardware processor may include a graphics processing unit (GPU) with a large number of processing units. In some implementations, the hardware processor may include a neural network processor. The system can include an imaging system and/or a radiotherapy system.

Some implementations can include a non-transitory computer readable medium having software instruction stored thereon that, when executed by a processor, cause the processor to perform operations according to the method mentioned above.

DETAILED DESCRIPTION

Figure 1:
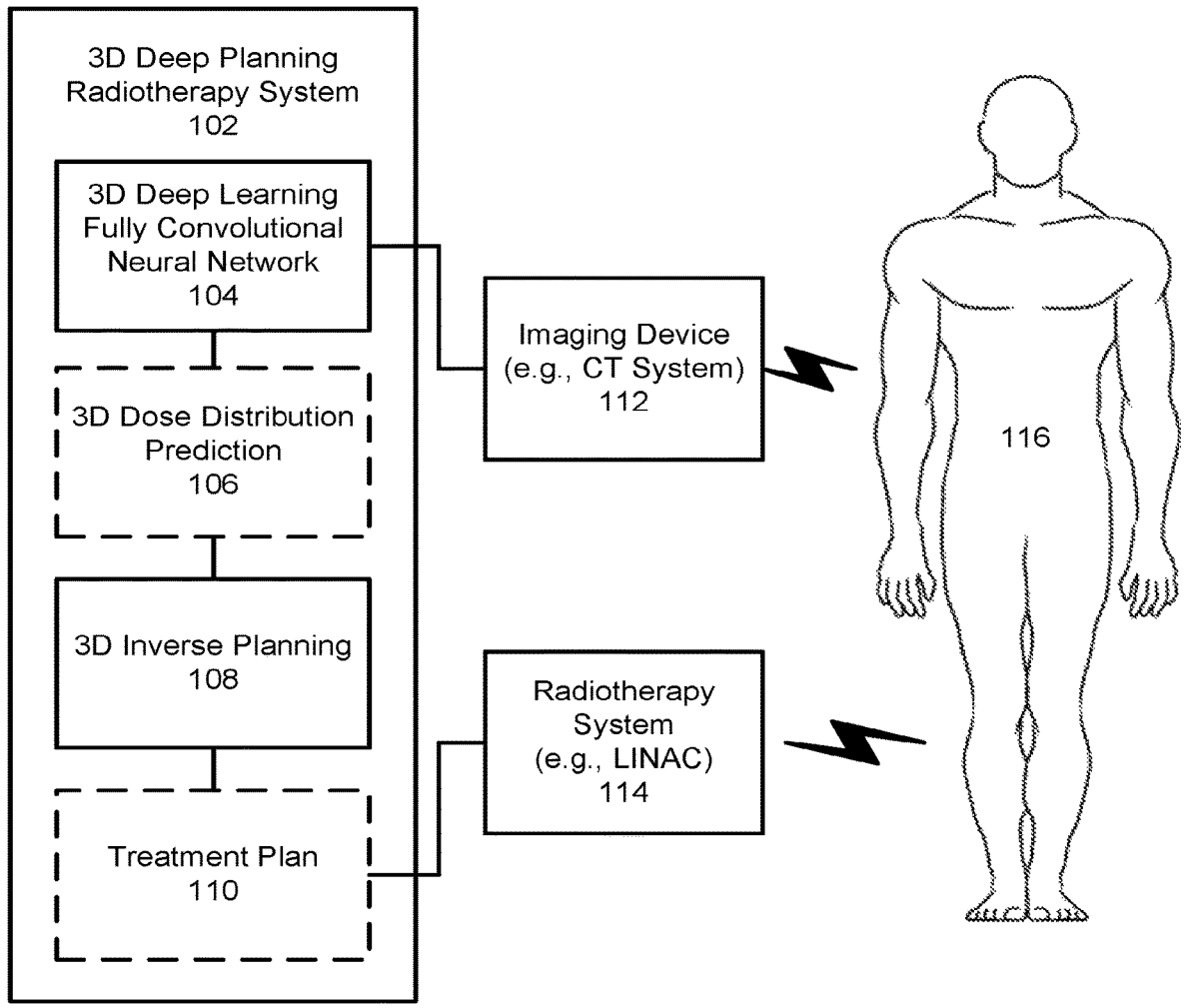
FIG. 1 is a diagram of an example radiotherapy environment in accordance with some implementations.

Some implementations include radiotherapy 3D deep planning systems and methods, which can include deep fully-convolutional neural networks configured to receive voxel data corresponding to a diseased organ as input, and to generate a 3D dose distribution to treat the diseased organ using radiation therapy. Some implementations can also include a system that can automatically design a clinically deliverable radiotherapy treatment plan for a patient by leveraging the discriminative power of deep learning and a knowledge database that includes clinically proven treatment plans used in prior treatments for various patients. The techniques described herein apply advanced deep learning to knowledge-based treatment planning (KBTP) for radiotherapy, where 3D information is fully utilized for dose prediction and planning. The implementations described herein may help address the problems and limitations with conventional techniques discussed above. Although the deep planning framework is general and the network structure can be kept the same as well, the FCNN may need to be trained for different cancer sites, for example the trained model for prostate cancer would be different from the trained model for lung cancer. It will be appreciated that this technique is not cancer-site-specific. Although we used prostate cancer in the preliminary study to demonstrate deep planning, implementations of the system and methods disclosed herein can be used for other cancer sites as well (such as liver, lung, head and neck, pelvis etc.).

Some implementations model the dose distribution prediction as a voxel-wise regression problem, where each voxel of the input consists of a vector of features that characterize physical properties and geometric relations among the Planning Target Volume (PTV) and adjacent Organs At Risk (OARs), i.e., normal organs to spare during treatment. The output from the model can include a predicted 3D dose distribution. Some implementations can have broad applications in clinical practice of treating cancer with radiotherapy. For example, as a visualization tool, some implementations can permit radiation oncologists to see a highly accurate dose distribution immediately after organ contouring, which can provide a good overview of the achievable dose. In another example, as a quality assurance (QA) tool, some implementations can give planners an objective measure to identify achievable normal organ sparing based on patient-specific information, thus guiding the planners to prioritize optimization objectives during planning. In yet another example, as an automated planning system, some implementations can be integrated into a clinical practice setting to improve efficiency, consistency and quality of treatment planning, and thus potentially help cure more cancer patients and improve their quality of life.

Some implementations utilize the 3D dose prediction with an inverse planning technique that incorporates predicted 3D dose distribution into the treatment planning process, and provide a treatment plan that is generated using optimization techniques to precisely control dose distribution in the clinically deliverable plan.

FIG. 1 is a diagram of an example radiotherapy environment 100 in accordance with some implementations. The environment includes a 3D deep planning radiotherapy system 102, an imaging device 112, a radiotherapy system 114, and a body 116 of a patient.

The 3D deep planning radiotherapy system 102 includes a 3D deep learning fully convolutional neural network (FCNN) 104, a 3D dose distribution prediction unit 106, a 3D inverse planning unit 108, and a treatment plan 110. In some implementations, the imaging device 112 can include a computed tomography (CT) system. Deep planning does not rely on any specific CT imaging systems. Any suitable CT imaging systems that are used in clinical practice can be used with the systems and methods described herein. As an example, a Philips Brilliance 16-slice large bore CT scanner can be used, with the output data in DICOM format. The imaging device 112 may provide imaging data for the body 116 that includes three-dimensional data. In some implementations, the imaging data may include data for one or more organs in the body 116. The imaging data may include diseased portions of an organ (e.g., cancerous portions) and health portions of the organ and/or surrounding parts of the body 116. In some implementations, the radiotherapy system 114 can include a linear accelerator (LINAC). For example, a TrueBeam LINAC developed by Varian Medical Systems (Palo Alto, Calif.) can be used. The treatment planning system can include the Eclipse treatment planning system by Varian. The treatment plan 110 can serve as input to the radiotherapy system 114 and can be used by the radiotherapy system 114 to direct the treatment of the body 116 of the patient. In some implementations, the 3D inverse planning unit 108 generates the treatment plan based on a 3D dose distribution prediction generated by the 3D deep learning FCNN 104. In some implementations, system 102 may be included as part of radiotherapy system 114. In some implementations, treatment plan 110 may include an electronic file that can command radiotherapy system 114 to apply radiation to the body 116 of the patient.

Figure 2:
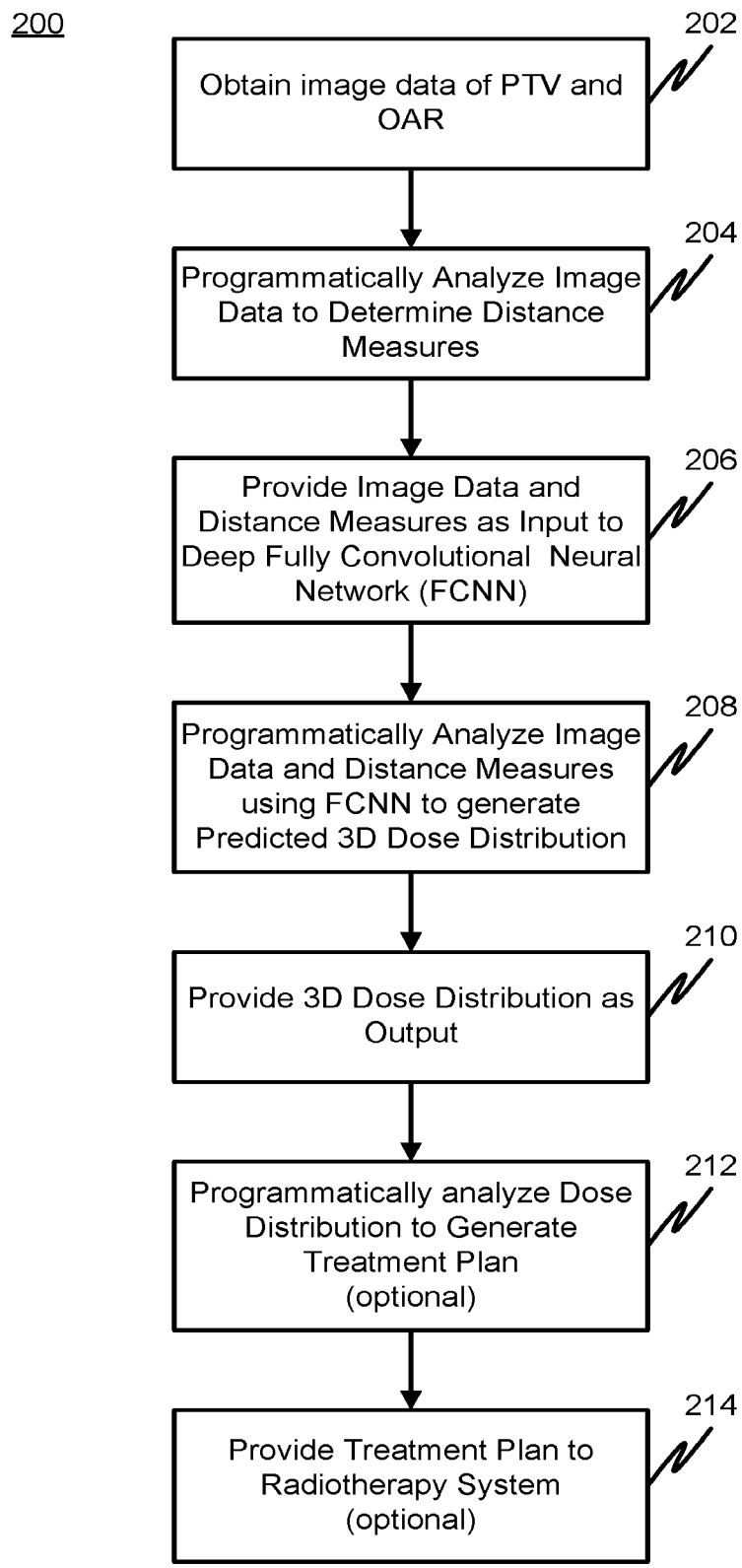
FIG. 2 is a flowchart of an example method for 3D dose distribution prediction and treatment planning using a fully convolutional neural network (FCNN) in accordance with some implementations.

FIG. 2 is a flowchart of an example method 200 for 3D dose distribution and treatment planning using a fully convolutional deep neural network (FCNN) in accordance with some implementations. Processing begins at 202, where one or more images (e.g., one or more 2D CT image "slices" of at least a portion of a body of a patient) are obtained. The images can include organ boundary indications input by a human user or by an automatic system. The image data can include image data corresponding to Planning Target Volume (PTV) and adjacent Organs At Risk (OARs). Processing continues to 204.

At 204, the image data and boundary indications are programmatically analyzed to generate measurement data for each voxel. In some implementations, the data for each voxel can include the feature channels listed in Table II. Other feature channels based on the type and location of the target volume can be used in a contemplated implementation. Processing continues to 206.

At 206, the image data and/or voxel data can be provided as input to a deep fully convolutional neural network (FCNN). For example, the 3D image data and/or 3D voxel image data can be provided to a FCNN such as that shown in FIGS. 1 and 3. The FCNN can include a deep FCNN that is a specific deep FCNN trained and configured for dose distribution prediction. Processing continues to 208.

Figure 3:
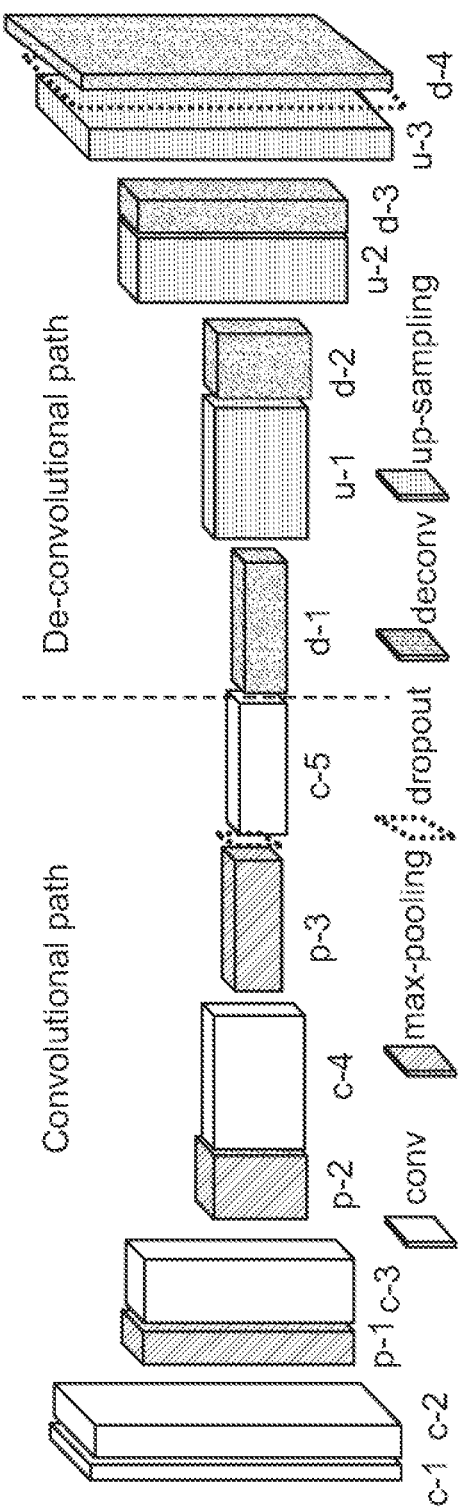
FIG. 3 is a diagram of an example FCNN to predict 3D dose distribution in accordance with some implementations.

At 208, the input data provided in 206 can be programmatically analyzed using the FCNN. For example, the input data can be processed by an FCNN as shown in FIG. 3 and described in detail below to produce a 3D dose distribution prediction as output. The input data can be processed as 2D slices of a 3D image or as a 3D image depending on available processing and memory resources. As compared to processing the 3D volume as a whole, the 2D slice-by-slice can be faster and more suitable when the hardware has limited GPU memory. On the other hand, the entire 3D image provides comprehensive information regarding patients, which could yield better performance than using 2D slices. Some implementations can include 2.5D, which includes a compromise between 2D and 3D. Processing continues to 210.

At 210, the 3D dose distribution prediction is provided as output. The output can be provided in the form of an electronic 3D dose distribution prediction file (e.g., in the DICOM-RT format), displayed on a display device, provided as an electronic file to another system, or provided as hard copy output (e.g., a physical print). Processing continues to 212.

At 212, the 3D dose distribution prediction output data is optionally programmatically analyzed to generate a treatment plan, e.g., an electronic file containing a treatment plan that is operable to cause a radiotherapy system to treat the body of a patient using radiation. For example, the 3D dose distribution prediction output data can be processed using an inverse planning technique as described in detail below. Processing continues to 214.

At 214, the treatment plan optionally is provided to a radiotherapy system. For example, an electronic file containing the treatment plan can be transmitted electronically to a radiotherapy system via wired or wireless network or connection. The radiotherapy system may apply radiation to the patient body based on the treatment plan.

In FIG. 2, various blocks (e.g., blocks 202-214) are illustrated as being performed sequentially. It will be appreciated however that these blocks may be re-arranged as convenient to suit particular embodiments and that these blocks or portions thereof may be performed concurrently in some embodiments. It will also be appreciated that in some examples various blocks may be eliminated, divided into additional blocks, and/or combined with other blocks.

Some implementations can include a software application for specialized medical equipment (e.g., radiotherapy systems, radiotherapy planning systems, imaging systems, etc,), desktop computers, laptop computers, and mobile devices (e.g., smartphones, tablet computing devices, etc.) that can be used by physicians and/or other health care professionals to perform 3D deep learning dose distribution prediction and/or treatment planning. The software application can also be provided as a web service accessible over a wired or wireless computer network.

In some implementations, the method, or portions of the method, can be initiated automatically by a device. For example, the method (or portions thereof) can be periodically performed or performed based on the occurrence of one or more particular events or conditions. For example, such events or conditions can include: obtaining one or more images that have been newly captured by, uploaded to, or otherwise accessible by a device (e.g., an imaging device such as a CT system as described herein), a predetermined time period having expired since the last performance of method 200, and/or one or more other events or conditions occurring which can be specified in settings of a device implementing method 200. In some implementations, such conditions can be previously specified by a user in stored custom preferences of the user (accessible by a device or method with user consent). In another example, an imaging device (e.g., a CT system) or other medical system can capture one or more images and can perform the method 200. In addition, or alternatively, an imaging device can send one or more captured images to an external system (e.g., a cloud computing system, a server, a mobile device, etc.) over a network, and the external system can process the images using method 200.

FIG. 3 is a diagram of an example FCNN to predict 3D dose distribution and plan radiotherapy treatment in accordance with some implementations. In some implementations, a 3D dose prediction can be generated using a deep fully convolutional neural network (FCNN). A neural network can include a hierarchical composite of multiple primary processing units called neurons. Contrary to the conventional multiple-layer perceptions (MLPs), where each neuron is directly collected to all neurons in a previous layer, the convolutional network assumes the input as images and exploits spatially local correlation by enforcing a local connectivity pattern between neurons of adjacent layers. The FCNN shown in FIG. 3 includes two pathways, in which contextual information can be aggregated via convolution (c) and pooling (p) in the convolutional path and full image resolution can be recovered via deconvolution (d) and up-sampling (u) in the deconvolutional path.

Specifically, let layer l be an $M^1 \times N^1$ matrix of neurons with $M^1$ rows and $N^1$ columns, and $n_{ij}^1$ represent a neuron located at (i, j). $x_{ij}$ and $y_{ij}$ are $K^1 \times 1$ vectors that correspond to the input and output of $n_{ij}$ respectively. $K^1$ is the number of features in layer 1.

Then the $k^{th}$ element of input vector to the following layer l+1 can be obtained as:

$$x_{ijk}^{l+1} = F_{rB}(\{Y_{si+i',sj+j'}^{l}\}_{0 \le i',j' < r}) \qquad (1)$$

where r is the size of local receptive field (LRF) that determines how many neurons from the layer l can be directly connected to $n_{ij}^{l+1}$, and s is the stride length that represents the offset between the neighboring LRFs. Depending on the type of layer, the function $F_{rs}$ could be a matrix multiplication for convolutional layer, a spatial max for pooling layer, or a nonlinear soft-max for output layer.

Some implementations can include an appropriate network architecture and effective training strategies to adapt to various patient-specific geometries. The neural network of the model shown in FIG. 3 contains 19 layers with 290,129 trainable parameters. Table I, below, describes architectural details of the FCNN In Table I, the left three columns list the layers in the convolutional path, while the right three columns list the layers in the deconvolutional path. For each layer, the first letter indicates the type of layer, with c standing for convolution layer, p for pooling layer, d for deconvolution layer and u for upsampling layer. The number after dash is the serial number for this type of layer, for example c-1 is the first convolution layer, c-2 is the 2nd convolution layer etc. The filter is the LRF size for this layer. For output, the first two numbers determine the dimension of the output of this layers (rows by columns), and the 3rd number is the number of channels for each element in the output.

TABLE 1

Architectural details of DoseNet.

| Conv | Filter | Output | Deconv | Filter | Output |
|------|--------|--------|--------|--------|--------|
| c-1  | 5 × 5  | 188 × 252 × 8 | d-1 | 5 × 5 | 21 × 29 × 64 |
| c-2  | 3 × 3  | 186 × 250 × 16 | u-1 | 2 × 2 | 42 × 58 × 64 |
| p-1  | 2 × 2  | 93 × 125 × 16 | d-2 | 4 × 4 | 45 × 61 × 32 |
| c-3  | 4 × 4  | 90 × 122 × 32 | u-2 | 2 × 2 | 90 × 122 × 32 |
| p-2  | 2 × 2  | 45 × 61 × 32 | d-3 | 4 × 4 | 93 × 125 × 16 |

TABLE 1-continued

Architectural details of DoseNet.

| Conv | Filter | Output | Deconv | Filter | Output |
|------|--------|--------|--------|--------|--------|
| c-4  | 4 × 4  | 42 × 58 × 64 | u-3 | 2 × 2 | 186 × 250 × 16 |
| p-3  | 2 × 2  | 21 × 29 × 64 | d-4 | 3 × 3 | 188 × 252 × 8 |
| c-5  | 5 × 5  | 17 × 25 × 64 | output | 5 × 5 | 192 × 256 × 1 |

Figure 4:
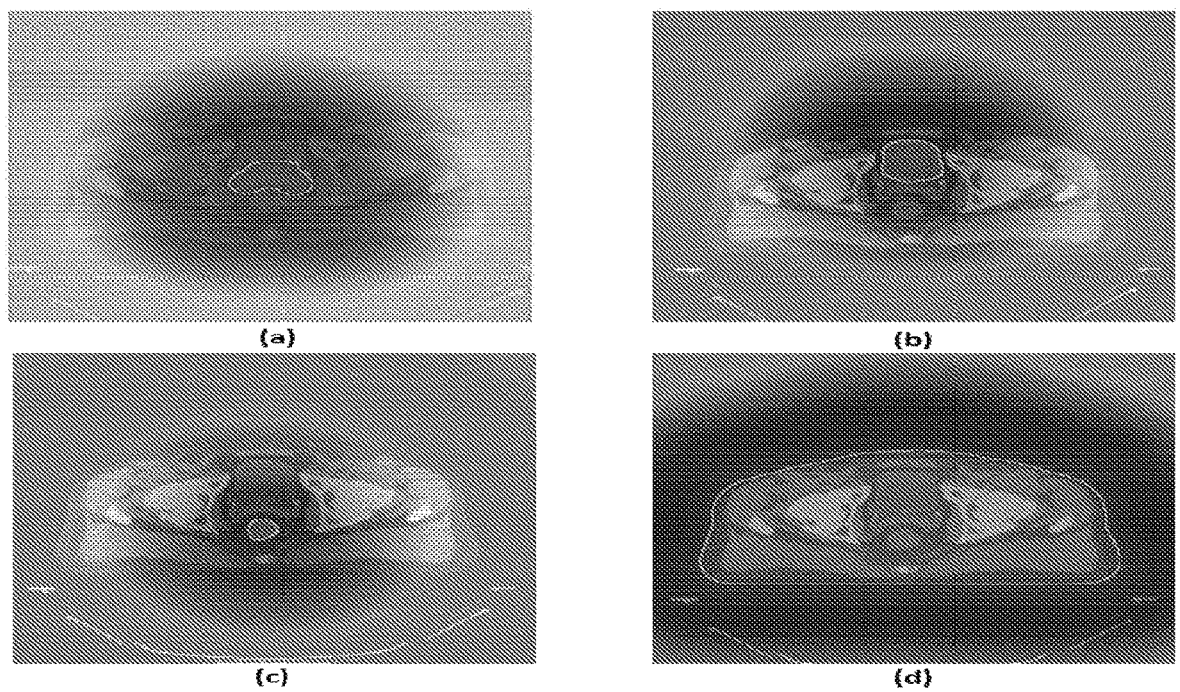
FIG. 4 shows diagrams of example computed tomography (CT) images and distance measures in accordance with some implementations.

Some implementations can include CT images and signed distance maps of each organ of interest in order to have the FCNN automatically learn features that are useful for dose prediction. For example, a signed distance map of an organ can be derived from the organ region that is contoured by radiation oncologist or automatic system, in which each voxel value can represent the Euclidean distance of this voxel to the closest organ surface in 3D space. The distance can be defined as positive if the voxel is within the organ, and negative if it is outside. FIG. 4 shows a four example signed distance maps of the following: (a) PTV; (b) bladder; (c) rectum; and (d) external body. Each distance map is superposed onto the corresponding CT image with organ outlined with green contour. Pseudo-color has been employed for better visualization. A voxel, as used herein, can include two or three dimensions (e.g., two dimensions in a 2D slice image and/or or a third dimension corresponding to a slice or a position in the third dimension) and one or more values corresponding to one or more input feature channels. For example, input feature channels for each voxel in a prostate cancer example are listed in Table II, below.

TABLE II

Input feature channels for each voxel.

| Feature | Symbol | Description |
|---------|--------|-------------|
| 1  | HU       | CT number (Hounsfield Unit) |
| 2  | $d_B$    | Distance to bladder |
| 3  | $d_{LFH}$| Distance to left femur head |
| 4  | $d_R$    | Distance to rectum |
| 5  | $d_P$    | Distance to prostate |
| 6  | $d_{RFH}$| Distance to right femur head |
| 7  | $d_E$    | Distance to external body |
| 8  | $d_{PTV}$| Distance to PTV |
| 9  | $d_{SV}$ | Distance to seminal vesicles |
| 10 | $d_{BW}$ | Distance to bladder wall |
| 11 | $d_{RW}$ | Distance to rectum wall |

In some implementations, e.g., due to limited GPU memory or other resource limitations, it may be very time-consuming, if not infeasible, to perform extensive convolution operations in 3D space in a deep neural network. Accordingly, some implementations can be configured to perform convolution in a 2D context, in that voxels in a same 2D slice are provided as input and the system outputs a corresponding dose prediction. Thus, a 3D patient volume can be processed slice-by-slice to generate a predicted 3D dose distribution. In some implementations, in the 2D slice-by-slice process, the different 2D slices can be processed in an FCNN in parallel. The dose prediction for one slice may not impact that for other slices because the relationship between any two slices has been taken into account in the calculated distance maps. In some implementations, where resource limitations mentioned above are not present, a system can perform the convolution and deconvolution operations in 3D space using the deep FCNN. Experiments reveal that the 2D slice-by-slice technique provides sufficient contextual information for the FCNN to reliably differentiate locally similar voxels and produce accurate dose predictions.

In a convolutional layer, the input of neuron n i+1 is the weighted sum of outputs of neurons in local receptive field, which is defined as filter size in Table I. Thus, equation (1) becomes:

$$x_{ijk}^{l+1} = \sum_{i'}^{r} \sum_{j'}^{r} (w_{i',j'}^l)^T y_{si+i',sj+j'}^l + b_k^l, \quad (2)$$

where $w_{i,j}$ is a $K^1 \times 1$ weight vector and $b_k^1$ is the bias in layer l, which are shared across neurons in the same layer. The activation function, which maps the input to the output of the neuron can be a tanh function or a sigmoid function ($f(x)=(1+e^{-x})^{-1}$) in the convolutional layer. However, in some implementations, a deep neural network trained with gradient descent can converge much faster when using Rectified Linear Units (ReLUs) as the activation function of a neuron, defined as:

$$y_{ijk}^{l+1} = f(x_{ijk}^{l+1}) = \max(0, x_{ijk}^{l+1}). \quad (3)$$

In some implementations, neurons within a layers not only have the same type of activation function, but can also have the same parameters of the activation function. The type of activation function depends on the type of layer, e.g., neurons in convolutional/deconvolutional layers use ReLU as the activation function, but the function parameters (weights and bias) of neurons in different layers can be different, which can be determined during the FCNN training procedure. Since neurons in a layer can have the same weights and bias, each feature map in this layer essentially performs a convolution of the input from the previous layer, with the kernel learned through back propagation.

The weight sharing, along with the local connectivity, significantly reduces the number of weights to be learned as compared to a fully-connected conventional networks. It also ensures that the same feature would be detected in various locations over the input images, which makes the convolutional networks translation invariant.

A pooling layer combines the output of convolutional layer in a local neighborhood into a statistic that summarizes the joint distribution of the feature over this local region. This downsampling operation makes the feature representation more compact and invariant to small changes of input images. Meanwhile, since features in the sub region are combined into a single output, pooling can reduce the computational load for the subsequent layers. While various other pooling strategies can also be used, some empirical results suggest that max-pooling that takes the maximum value as the output in a sub-region gives superior performance in most cases. Accordingly, some implementations include max-pooling.

With the successive convolution and pooling layers, the convolutional path can integrate contextual information from regional to global scales, resulting in reduced resolution in the output layer. In contrast, dose prediction calls for assigning each voxel a dose value in combination with full-resolution output. In order to address this conflict between multi-scale information aggregation and full-resolution voxel-wise regression, a strategy of using up-sampling and deconvolutional layers to recover lost resolution while carrying over the global perspective from pooling layers is implemented.

The up-sampling layer performs the reverse operation of pooling and reconstructs the original size of activation, and the deconvolutional layer densifies the coarse activation map obtained from up-sampling through swapping the forward and backward passes of a convolution, thus a single input activation is projected into multiple outputs after deconvolution, yielding an enlarged and dense feature map. Echoing the convolutional path where image information is aggregated from fine details to global concept, a hierarchical structure of deconvolutional layers is used to recover image details at different levels, with the lower layers encoding overall image information and higher layers capturing fine details regarding patient-specific anatomies. In this way, the network can take both global information and fine details into account for 3D dose prediction. Upsampling is the reverse procedure of pooling, in which the output is enlarged. The activation function for neurons in the deconvolutional layers is ReLU, can be the same as convolutional layers.

A traditional convolutional network typically can include several alternations between convolutional layers and pooling layers, followed by one or more fully-connected layers with the outputs predicting the probability of being in one of the several possible classes. Since every output neuron is directly connected to all the input neurons in a fully-connected layer, this type of network architecture loses spatial information and cannot be directly used for a regression problem. In order to resolve this issue, the input image is divided into patches and patch-wise image regression is carried out using convolutional network with fully-connected layers. Since the patch regression only considers local context, advanced post-processing techniques are usually used to further improve the performance on the entire image.

In some implementations of the present disclosure, the fully-connected layer can be replaced by another convolutional layer as the output. The LRF size for the output layer is set as 1×1, and the activation function is a sigmoid function:

$$y_{ij}^L = sig(x_{ij}^L) = \frac{1}{1 + e^{-x_{ij}^L}}, \quad (4)$$

where L is the total number of layers in the network.

Some implementations can be considered as representing a complex end-to-end regression function that transforms the patient-specific information in 4D form (e.g., three dimensional location information along with one or more voxel feature channel values) to its corresponding dose map. Learning this complex regression function requires the estimation of network parameters θ={w1, b1, w2, b2, . . . }, which is achieved through back-propagation by minimizing a loss function between the predicted dose maps F (X; θ) and the corresponding previously used "good" clinical plans D. Given a set of patient information {Xn} and their corresponding plans {Dn}, the Mean Squared Error (MSE) is used as the loss function:

$$L(\theta) = \frac{1}{N} \sum_{n=1}^{N} [D_n - F(X_n; \theta)]^2, \quad (5)$$

where N is the number of training samples. In general, any measures that quantify the difference between the predicted dose map and the actual clinical plan can be potentially used as loss functions. In addition to or as an alternative to MSE, mean absolute error (MAE) can be used.

Training a deep network model with a limited number of samples can be a challenging task. As described above, the example model shown in FIG. 3 has 19 layers and 290,129 parameters to be learned. In a preliminary study, data of 21 prostate patients was included in the training set, which is considered a relatively small training set as compared to the size of the network. In order to address this issue, some implementations can employ the following strategies to improve the efficiency of network training while reducing overfitting.

Proper initialization of network weights can be important to a deep network because a bad initialization can slow down or even stall the learning procedure due to the instability of gradient. Some implementations can include a random initialization strategy, called Xavier initialization. In this method, the initial bases are set as 0, and the initial weights from layer l to layer l +1 wl,l+1 are randomly selected from $$w_{l,l+1} \sim U\left[-\frac{\sqrt{6}}{\sqrt{N_l + N_{l+1}}}, \frac{\sqrt{6}}{\sqrt{N_l + N_{l+1}}}\right], \quad (6)$$

where U[⁻a, a] is the uniform distribution in the interval (⁻a, a) and $N_l$ is the number of neurons in the layer 1. This normalized initialization keeps the activation and back-propagated gradients in a controlled level when moving up and down the network. This initialization strategy controls the magnitude of activation and back-propagated gradients such that they are not too big nor too small, and thus can help ensure numeric stability when training the deep FCNN.

Stochastic gradient descent (SGD) with mini-batch is usually employed as the optimization algorithm for neural network training. It is well known that learning rate is one of the critical hyper-parameters that have a significant impact on classification performance. However, selecting proper learning rate and strategy can be fairly challenging. One commonly used strategy is to anneal the learning rate at each iteration t as $_{r0}$α+t where α and $_{r0}$ dictate the initial learning rate and the time when the annealing starts respectively, but it tends to have slow convergence when the loss function is highly sensitive to some directions in parameter space while insensitive to others. The momentum algorithm can mitigate this issue, but with the expense of introducing another hyper-parameter.

Some implementations can include an Adam optimization algorithm, or adaptive moments, to adjust the learning rate based on the first and the second-order moments of the gradient at each iteration. Here the momentum is incorporated as an estimate of the first moment and the effective step size at each iteration t depends on the ratio between the bias-corrected first and second-order moments as $\Delta t = \alpha \cdot \hat{m}_t / \sqrt{\hat{v}_t}$, with a smaller value indicating that there is greater uncertainty about whether the direction of m^t corresponds to the direction of the true gradient. Adam can be fairly robust to the choice of hyper-parameters, and the learning rate a can be set, for example, as 0.003 to speed up the training procedure in some implementations.

Some implementations can include batch normalization to reduce the internal covariate shift by normalizing the input distribution of one or more layers to the standard Gaussian distribution for each training mini-batch. For this purpose, some implementations can include a batch normalization layer added to the output of one or more convolutional and de-convolutional layers. The batch normalization can be performed over locations in the same feature map such that different elements in the same map are normalized in the same way.

Some implementations can include dropout, which can provide a powerful and computationally inexpensive way to reduce overfitting when training a very deep FCNN model with limited data. This technique sets the output of one or more neurons in a given layer to zero. For example, neurons may be set to zero randomly, e.g., with a probability p, that can provide a particular dropout rate. These "dropped out" neurons do not contribute to the forward pass or the back-propagation. The subset of disabled or dropped-out neurons is drawn independently for each mini-batch and forms a different network architecture, then dropout trains the ensemble of all sub-networks that have different architectures but share weights in one epoch. In this way, a neuron cannot rely on the presence of particular other neurons and it is, therefore, forced to learn more robust features that are useful among different random subsets. This can make a trained FCNN more robust and can improve the generalization ability.

Some implementations can include dropout with p=0.5 before conv5 and deconv4 layers in FIG. 3. Although dropout roughly doubles the number of iterations for convergence, our experiments have shown that dropout can reduce overfitting substantially.

The present inventors retrospectively collected data for 60 prostate cancer patients in a preliminary study, in which 28 patients were randomly selected for FCNN training and the remaining 32 patients for independent testing to compare with a technology developed by McIntosh et al. from Princess Margaret Cancer Centre (PMCC technique). The CT images were acquired in the axial plane, with in-plane spatial resolution ranging from 0.97 mm×0.97 mm to 1.37 mm×1.37 mm while the slice thickness was fixed as 3 mm. Each CT set included 512×512 voxels in the axial plane with variable volume extent depending on patient size. All patients were treated with the RapidArc technique with prescription dose of 45 Gy delivered in 28 fractions. Treatment plans were designed by dosimetrists with a commercial treatment planning system Eclipse (Varian Medical Systems, Palo Alto, Calif.), and reviewed by multiple experts before being used for treatment. The dose calculation grid was resampled to 2.5 mm×2.5 mm×3 mm in order to speed up dose calculation procedure when generating treatment plans.

The performance of an example implementation, as shown in FIG. 3, was assessed by comparing the predicted dose distribution with the corresponding clinically-proven plans created by human planners (medical dosimetrists). The voxel-wise dose difference on between the clinical plan and prediction: $\Delta D=D_{clin}-D_{pred}$ was calculated and the average dose on PTV was compared. Comparisons also included the dose sparing criteria on OARs.

Gamma analysis was also employed for comparison. Gamma analysis is a commonly used quantitative similarity evaluation technique in radiation oncology, when comparing an implementation of the present disclosure to the PMCC technique. The Gamma between a dose-to-voxel da,r and a reference dose distribution da is defined as:

$$\gamma(\tilde{d}_{a,r}, d_a) = \min_{r' \in M} \sqrt{\frac{|r-r'|^2}{\alpha^2} + \frac{|\tilde{d}_{a,r}-d_{a,r'}|^2}{\beta^2}}, \quad (7)$$

where $r \in M$ is a search over a neighborhood of voxels in the reference dose $d_\alpha$, $\alpha$ is the spatial distance threshold criterion and $\beta$ is the dose difference threshold criterion. The Gamma pass rate between two distribution, $\Gamma(d_{\alpha,r}, d_\alpha)$, is the percentage of voxels with $(d_{\alpha,r}, d_\alpha) \leq 1$, which is the percentage of voxels with dose similar enough to at least one voxel in a spatial neighborhood in the reference dose distribution. We set Gamma at 80% of prescription dose with a tolerance of $\beta$=5% and a neighborhood of $\alpha$=5 mm.

The first evaluation was conducted using a four-fold cross-validation procedure. The 28 training cases were randomly divided into four equal-sized groups. One group (7 patients) was retained as the test set, and the remaining three groups (21 patients) were used as training set to train the FCNN implementation. The trained FCNN was then applied to each test patient data to generate a predicted dose distribution.

Figure 5:
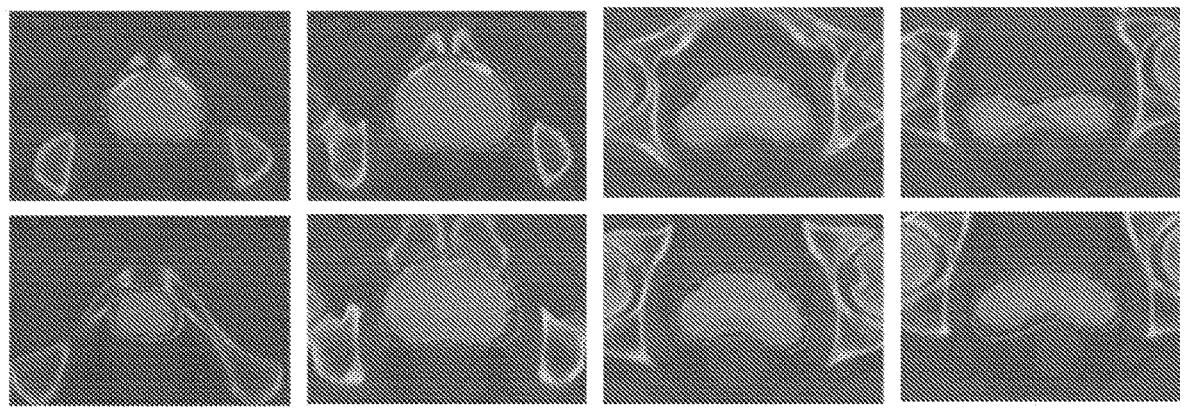
FIG. 5 shows diagrams of example images with performance comparison.
Figure 6:
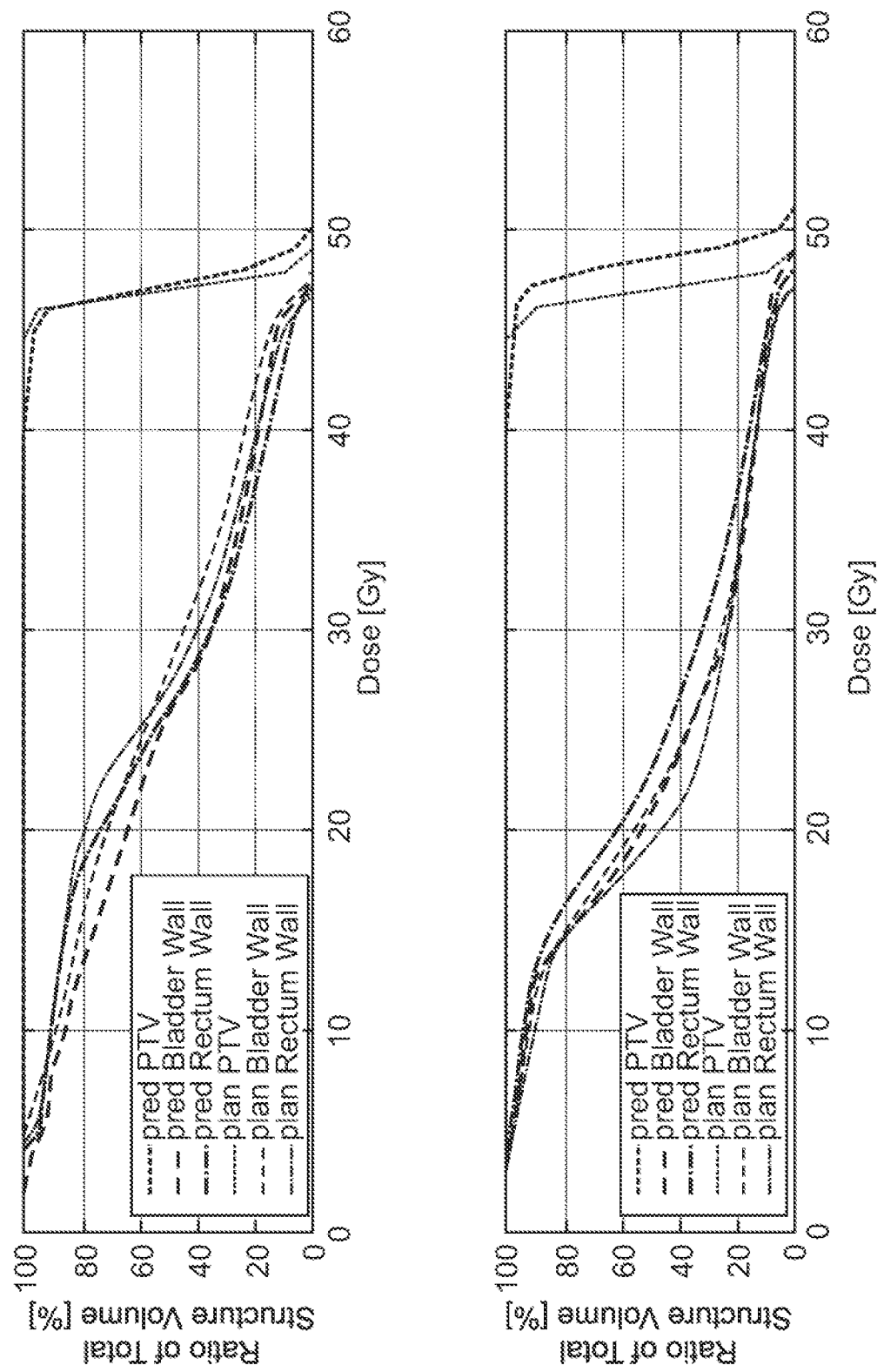
FIG. 6 shows graphs of performance comparisons.

The average predicted dose on PTV was found to be 46.5±1.15 Gy, while the planned dose was 46.8±0.24 Gy. The average voxel-wise dose difference on PTV was 4.73%. FIG. 5 shows some examples where the yellow region is the PTV, the green dash line represents the prescribed 45 Gy isodose line from clinical plans, and the red solid line is the predicted 45 Gy isodose line. FIG. 6 shows two examples of DVH comparisons for PTV and two OARs (Rectum Wall and Bladder Wall). Table III below summarizes the dose constraints on these two OARs.

TABLE III

Dose constraint comparison on rectum wall and bladder wall.

| OAR Constraints | | Clinical Plans | DoseNet |
|---|---|---|---|
| Bladder Wall | V30 < 50% | 29.5% | 32.0% |
| | V40 < 30% | 17.4% | 16.9% |
| Rectum Wall | V30 < 50% | 28.0% | 33.0% |
| | V40 < 30% | 15.9% | 12.6% |

The performance of the example FCNN implementation of the disclosed subject matter was evaluated on an independent testing dataset that included 32 prostate patients, and found that the example FCNN yielded an average Gamma pass rate of 95.39%, which compares favorably to the techniques developed by McIntosh et al. from PMCC. For the PMCC technique, a multiple-atlas-based method for automated dose prediction was developed that relies on hand-crafted image-patch features and contextual atlas regression forest. The average Gamma pass rate was reported as 86.83%. Because that technique may require comparing the new image with each of the atlas image in the training set, the average run-time was as slow as 6 minutes. In contrast, with the techniques described herein, it only took about 12 seconds for the FCNN implementation of FIG. 3 to predict a 3D dose distribution given patient-specific information. These results are summarized as Table IV below. Although the Gamma pass rates are not directly comparable since the patient data used in each study were different, this study does illustrate that the FCNN implementation of FIG. 3 is a highly accurate and efficient system for automated treatment planning for radiotherapy.

TABLE IV

Comparison with PMCC technique.

|  | Gamma pass rate | Run-time/patient |
|---|---|---|
| PMCC | 86.83% | 6 minutes |
| DoseNet | 95.39% | 12 seconds |

Although a deep learning model typically requires a large amount of training data, very good performance was still achieved in the example implementation described herein by designing network architecture and employing training strategies to ensure effective and efficient learning with limited patient data. The disclosed techniques do not require any inter-patient patient image registration and can directly predict the dose distribution from CT images and geometric relationships among different organs. Compared to the atlas-based method with patch fusion developed in PMCC, the example FCNN implementation offered a highly accurate dose prediction. The atlas-based method may rely on patch comparison to find similar atlas candidates. A small patch only represents local information and using features extracted from limited patch information may suffer from large redundancy in the data and reduce the discriminative power. In contrast, the FCNN of the present disclosure automatically learns hierarchical features at different scales and complexities from a full input space.

Another advantage of some implementations is that dose prediction is rapid when new patient data is provided. Although training an FCNN implementation can take several days, the training may only need to be done once and acceleration can be possible with a system having more powerful GPU or multiple GPUs.

The FCNN implementation of FIG. 3 took about 12 seconds to predict a 3D dose distribution for each new patient. In contrast, because the atlas-based method needs to compare the new patient to every case in the atlas database to find the most similar one, the run-time can be rather slow (e.g., 6 minutes).

Another advantage that can be provided by some implementations can include a highly scalable system that can easily accommodate large amounts of training data. It is well known that deep neural network models can greatly benefit from large training data sets due to their high model capacity. Thus, it is expected that the accuracy of some implementations can be further improved when more training data is utilized. While the training time may be increased with more training data, the time for dose prediction remains the same because the number of trainable parameters in the FCNN implementation may not be changed. On the other hand, the run-time for the atlas-based method may be directly proportional to the number of atlases used. Further, in an implementation of the FCNN described herein, only the learned parameters may need to be deployed, whereas the atlas-based method may require all the training data to be stored when being applied to the new patient, which could be cumbersome and may occupy more storage space (e.g., on hard disk, etc.).

Some implementations can include a fully automated treatment planning process (e.g., 3D inverse planning 108) can be included in a deep planning framework 102 to convert the predicted 3D dose distribution data 106 to a treatment plan 110 that can be clinically delivered through a treatment device (e.g., 114). Currently, some KBTP systems employ predicted 2D dose-volume histograms (DVHs) on OARs to guide the inverse planning procedure; however, estimating the target DVH objectives by utilizing prior knowledge of achievable DVHs on OARs has been shown to be sub-optimal because DVH summarizes the 3D dose distribution into a 2D graph. As the result, these KBTP systems may merely provide an initial plan to a planner and heavy human interactions may still be needed to achieve a good plan.

Figure 8:
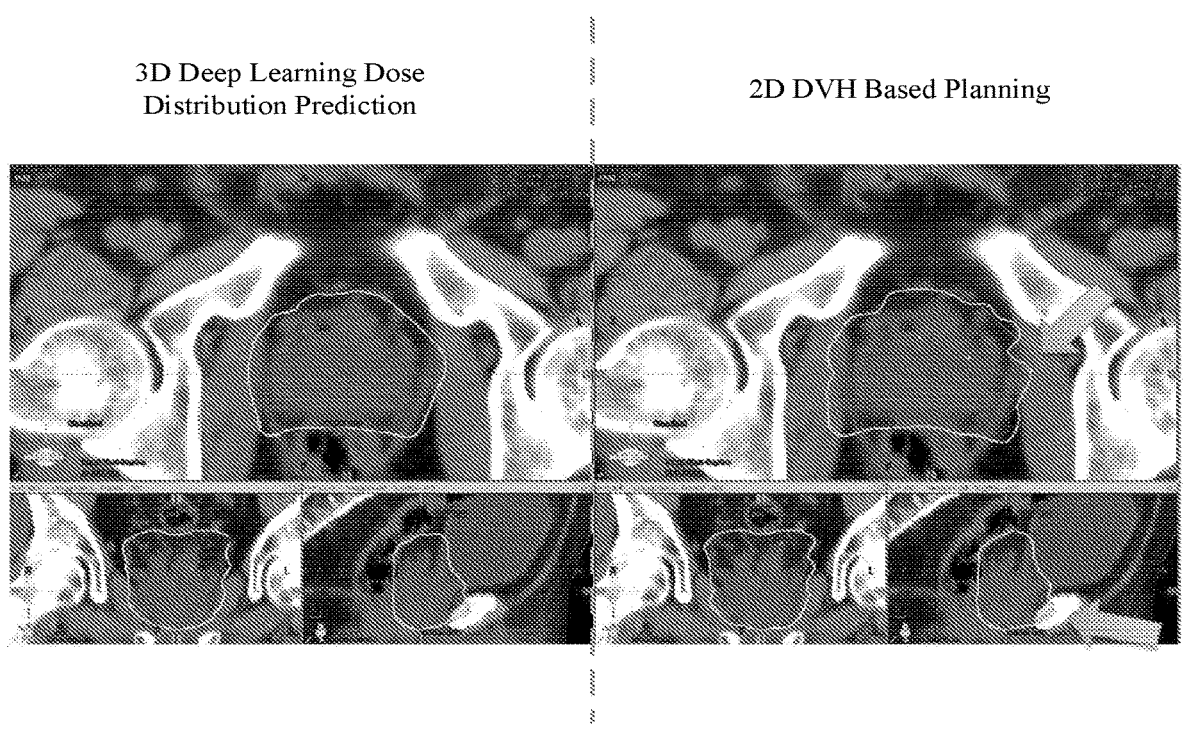
FIG. 8 shows images of example performance of 3D deep learning treatment planning in accordance with some implementations.

By leveraging the prediction capacity of the FCNN as disclosed herein, a 3D inverse planning strategy can incorporate the predicted 3D dose distribution into the planning procedure. In a proof-of-concept study, the present inventors compared the 3D inverse planning of the present disclosure with 2D DVH based planning on one patient in the task of reproducing a clinical plan. FIG. 8 shows a side-by-side comparison of these two techniques, in which the red region is the 45 Gy dose region in the clinical plan, and the green line is the same dose line generated by 3D dose and 2D DVH planning, respectively. Table V compares the OAR constraints. These results show that the plan generated by 3D inverse planning is more similar to the clinical plan than the one from 2D DVH based planning.

TABLE V

Dose constraint comparison between 2D
DVH based and 3D dose based inverse planning.

| OAR Constraints | | Clinical Plans | 2D DVH | 3D Dose |
|---|---|---|---|---|
| Bladder Wall | V30 < 50% | 16.19% | 15.53% | 15.20% |
|  | V40 < 30% | 9.67% | 10.15% | 9.51% |
| Rectum Wall | V30 < 50% | 29.01% | 31.60% | 29.86% |
|  | V40 < 30% | 18.47% | 20.17% | 18.48% |

Figure 7:
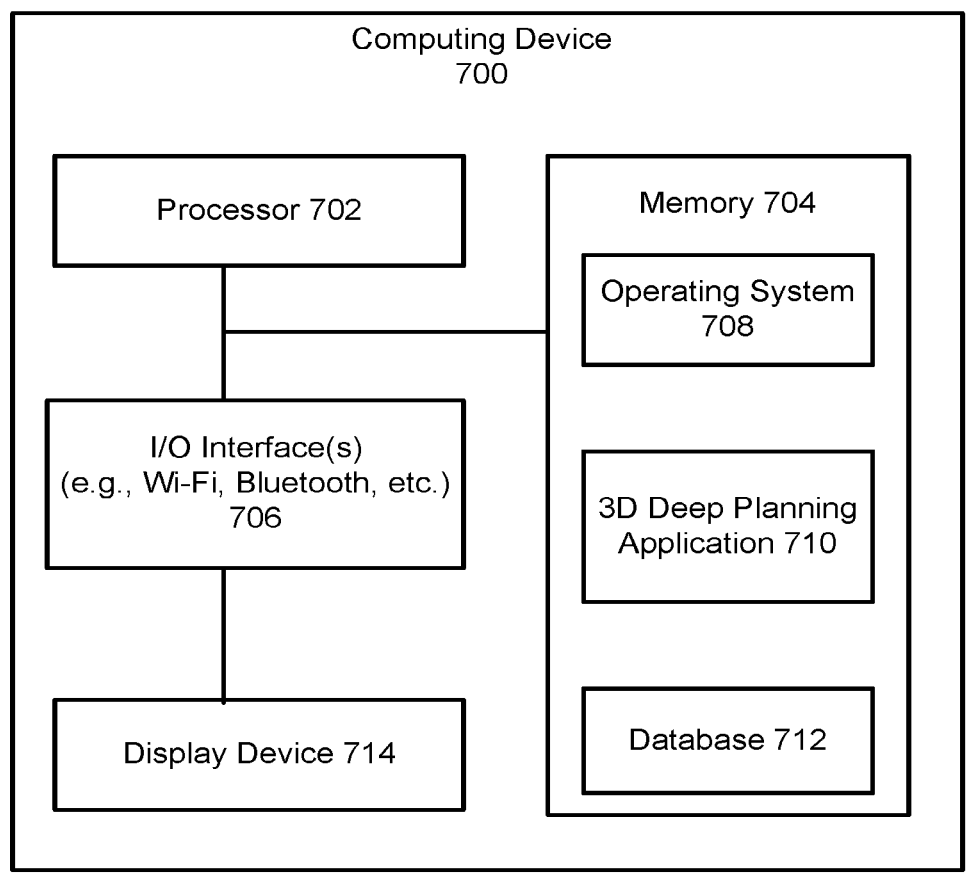
FIG. 7 is a diagram of an example system configured to perform 3D deep learning dose distribution prediction and treatment planning in accordance with some implementations.

FIG. 7 is a block diagram of an example computing device 700 which may be used to implement one or more features described herein. In one example, device 700 may be used to implement a computer device, e.g., a radiotherapy imaging, planning or treatment device (e.g., 102 of FIG. 1), and perform appropriate method implementations described herein. Device 700 can be any suitable computer system, server, or other electronic or hardware device. For example, the device 700 can be a mainframe computer, desktop computer, workstation, portable computer, or medical device. In some implementations, device 700 includes a processor 702, a memory 704, and input/output (I/O) interface 706.

Processor 702 can be one or more processors and/or processing circuits to execute program code and control basic operations of the device 700. A "processor" includes any suitable hardware and/or software system, mechanism or component that processes data, signals or other information. A processor may include a system with a general-purpose central processing unit (CPU), multiple processing units, dedicated circuitry for achieving functionality, or other systems. Processing need not be limited to a particular geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory.

Memory 704 is typically provided in device 700 for access by the processor 702, and may be any suitable processor-readable storage medium, e.g., random access memory (RAM), read-only memory (ROM), Electrical Erasable Read-only Memory (EEPROM), Flash memory, etc., suitable for storing instructions for execution by the processor, and located separate from processor 702 and/or integrated therewith. Memory 704 can store software operating on the server device 700 by the processor 702, including an operating system 708, one or more applications 710, e.g., a 3D deep learning dose distribution prediction and treatment planning application and application data 720. In some implementations, applications 710 can include instructions that enable processor 702 to perform the functions described herein, e.g., some or all of the method of FIG. 2.

For example, applications 710 can include a 3D deep learning dose distribution prediction and/or treatment planning application, which as described herein can provide a 3D radiotherapy dose distribution prediction based on 3D imaging (e.g., a CT scan) and, optionally, a treatment plan. Any of software in memory 704 can alternatively be stored on any other suitable storage location or computer-readable medium. In addition, memory 704 (and/or other connected storage device(s)) can store images, and other instructions and data used in the features described herein. Memory 704 and any other type of storage (magnetic disk, optical disk, magnetic tape, or other tangible media) can be considered "storage" or "storage devices."

In various implementations, applications 710 can include a machine-learning application. The machine-learning application may utilize Bayesian classifiers, support vector machines, neural networks, or other learning techniques. In some implementations, machine-learning application may include a trained model, an inference engine, and data. In some implementations, data may include training data, e.g., data used to generate trained model. For example, training data may include any type of data such as text, images, audio, video, etc. Training data may be obtained from any source, e.g., a data repository specifically marked for training, data for which permission is provided for use as training data for machine-learning, etc. In implementations where one or more users permit use of their respective user data to train a machine-learning model, e.g., trained model, training data may include such user data. In implementations where users permit use of their respective user data, data may include permitted data such as images (e.g., photos or other user-generated images), communications (e.g., e-mail; chat data such as text messages, voice, video, etc.), documents (e.g., spreadsheets, text documents, presentations, etc.)

In some implementations, data may include collected data such as CT image data, etc. In some implementations, training data may include synthetic data generated for the purpose of training, such as data that is not based on user input or activity in the context that is being trained, e.g., data generated from simulated computer-generated images, etc. In some implementations, machine-learning application excludes data. For example, in these implementations, the trained model may be generated, e.g., on a different device, and be provided as part of machine-learning application. In various implementations, the trained model may be provided as a data file that includes a model structure or form, and associated weights. Inference engine may read the data file for trained model and implement a neural network with node connectivity, layers, and weights based on the model structure or form specified in trained model.

Machine-learning application also includes a trained model. In some implementations, the trained model may include one or more model forms or structures. For example, model forms or structures can include any type of neural-network, such as a linear network, a deep neural network that implements a plurality of layers (e.g., "hidden layers" between an input layer and an output layer, with each layer being a linear network), a convolutional neural network (e.g., a network that splits or partitions input data into multiple parts or tiles, processes each tile separately using one or more neural-network layers, and aggregates the results from the processing of each tile), a sequence-to-sequence neural network (e.g., a network that takes as input sequential data, such as words in a sentence, frames in a video, etc. and produces as output a result sequence), etc. The model form or structure may specify connectivity between various nodes and organization of nodes into layers. For example, nodes of a first layer (e.g., input layer) may receive data as input data or application data. Such data can include, for example, one or more voxels per node, e.g., when the trained model is used for 3D or 4D image analysis. Subsequent intermediate layers may receive as input output of nodes of a previous layer per the connectivity specified in the model form or structure. These layers may also be referred to as hidden layers. A final layer (e.g., output layer) produces an output of the machine-learning application. For example, the output may be a 3D dose distribution prediction, treatment plan, etc. depending on the specific trained model. In some implementations, model form or structure also specifies a number and/ or type of nodes in each layer.

In different implementations, trained model can include a plurality of nodes, arranged into layers per the model structure or form. In some implementations, the nodes may be computational nodes with no memory, e.g., configured to process one unit of input to produce one unit of output. Computation performed by a node may include, for example, multiplying each of a plurality of node inputs by a weight, obtaining a weighted sum, and adjusting the weighted sum with a bias or intercept value to produce the node output. In some implementations, the computation may include applying a step/ activation function to the adjusted weighted sum. In some implementations, the step/ activation function may be a non-linear function. In various implementations, computation may include operations such as matrix multiplication. In some implementations, computations by the plurality of nodes may be performed in parallel, e.g., using multiple processors cores of a multicore processor, using individual processing units of a GPU, or special-purpose neural circuitry. In some implementations, nodes may include memory, e.g., may be able to store and use one or more earlier inputs in processing a subsequent input. For example, nodes with memory may include long short-term memory (LSTM) nodes. LSTM nodes may use the memory to maintain "state" that permits the node to act like a finite state machine (FSM). Models with such nodes may be useful in processing sequential data, e.g., words in a sentence or a paragraph, frames in a video, speech or other audio, etc.

In some implementations, trained model may include embeddings or weights for individual nodes. For example, a model may be initiated as a plurality of nodes organized into layers as specified by the model form or structure. At initialization, a respective weight may be applied to a connection between each pair of nodes that are connected per the model form, e.g., nodes in successive layers of the neural network. For example, the respective weights may be randomly assigned, or initialized to default values. The model may then be trained, e.g., using data, to produce a result.

For example, training may include applying supervised learning techniques. In supervised learning, the training data can include a plurality of inputs (e.g., a set of images and/or voxel data) and a corresponding expected output for each input (e.g., 3D dose distribution prediction). Based on a comparison of the output of the model with the expected output, values of the weights are automatically adjusted, e.g., in a manner that increases a probability that the model produces the expected output when provided similar input.

In some implementations, training may include applying unsupervised learning techniques. In unsupervised learning, only input data may be provided and the model may be trained to differentiate data, e.g., to cluster input data into a plurality of groups, where each group includes input data that are similar in some manner. For example, the model may be trained to predict 3D dose distribution from CT image data.

In some implementations, unsupervised learning may be used to produce knowledge representations, e.g., that may be used by machine-learning application. In various implementations, a trained model includes a set of weights, or embeddings, corresponding to the model structure. In implementations where data is omitted, machine-learning application may include trained model that is based on prior training, e.g., by a developer of the machine-learning application, by a third-party, etc. In some implementations, trained model may include a set of weights that are fixed, e.g., downloaded from a server that provides the weights.

Machine-learning application also includes an inference engine. Inference engine is configured to apply the trained model to data, such as application data, to provide an inference. In some implementations, inference engine may include software code to be executed by processor. In some implementations, inference engine may specify a circuit configuration (e.g., for a programmable processor, for a field programmable gate array (FPGA), etc.) enabling a processor to apply the trained model. In some implementations, inference engine may include software instructions, hardware instructions, or a combination. In some implementations, inference engine may offer an application programming interface (API) that can be used by an operating system and/or other applications to invoke inference engine, e.g., to apply trained model to application data to generate an inference.

Machine-learning application may provide several technical advantages. For example, when trained model is generated based on unsupervised learning, trained model can be applied by inference engine to produce knowledge representations (e.g., numeric representations) from input data, e.g., application data. In some implementations, knowledge representations generated by machine-learning application may be provided to a different device that conducts further processing, e.g., over a network. In such implementations, providing the knowledge representations rather than the images may provide a substantial technical benefit, e.g., enable faster data transmission with reduced cost.

In some implementations, machine-learning application may be implemented in an offline manner. In these implementations, trained model may be generated in a first stage, and provided as part of machine-learning application. In some implementations, machine-learning application may be implemented in an online manner. For example, in such implementations, an application that invokes machine-learning application (e.g., operating system, one or more of other applications) may utilize an inference produced by machine-learning application, e.g., provide the inference to a user, and may generate system logs (e.g., if permitted by the user, an action taken by the user based on the inference; or if utilized as input for further processing, a result of the further processing). System logs may be produced periodically, e.g., hourly, monthly, quarterly, etc. and may be used, with user permission, to update trained model, e.g., to update embeddings for trained model.

In some implementations, machine-learning application may be implemented in a manner that can adapt to particular configuration of device on which the machine-learning application is executed. For example, machine-learning application may determine a computational graph that utilizes available computational resources, e.g., processor. For example, if machine-learning application is implemented as a distributed application on multiple devices, machine-learning application may determine computations to be carried out on individual devices in a manner that optimizes computation. In another example, machine-learning application may determine that processor includes a GPU with a particular number of GPU cores (e.g., 1000) and implement the inference engine accordingly (e.g., as 1000 individual processes or threads).

In some implementations, machine-learning application may implement an ensemble of trained models. For example, trained model may include a plurality of trained models that are each applicable to same input data. In these implementations, machine-learning application may choose a particular trained model, e.g., based on available computational resources, success rate with prior inferences, etc. In some implementations, machine-learning application may execute inference engine such that a plurality of trained models are applied. In these implementations, machine-learning application may combine outputs from applying individual models, e.g., using a voting-technique that scores individual outputs from applying each trained model, or by choosing one or more particular outputs. Further, in these implementations, machine-learning application may apply a time threshold for applying individual trained models (e.g., 0.5 ms) and utilize only those individual outputs that are available within the time threshold. Outputs that are not received within the time threshold may not be utilized, e.g., discarded. For example, such approaches may be suitable when there is a time limit specified while invoking the machine-learning application, e.g., by operating system or one or more applications.

In different implementations, machine-learning application can produce different types of outputs. In some implementations, machine-learning application may produce an output based on a format specified by an invoking application, e.g. operating system or one or more applications. In some implementations, an invoking application may be another machine-learning application. For example, such configurations may be used in generative adversarial networks, where an invoking machine-learning application is trained using output from machine-learning application and vice-versa.

I/O interface 706 can provide functions to enable interfacing the computing device 700 with other systems and devices. For example, network communication devices, storage devices (e.g., memory and/or database 106), and input/output devices can communicate via interface 706. In some implementations, the I/O interface 706 can connect to interface devices including input devices (keyboard, pointing device, touchscreen, microphone, camera, scanner, etc.) and/or output devices (display device, speaker devices, printer, motor, etc.). Display device 714 is one example of an output device that can be used to display images and other data, e.g., one or more images, 3D dose distribution predictions, and treatment plans provided by an application as described herein. Display device 714 can be connected to device 700 via local connections (e.g., display bus) and/or via networked connections and can be any suitable display device, some examples of which are described below.

For ease of illustration, FIG. 7 shows one block for each of processor 702, memory 704, I/O interface 706, and software blocks 708 and 710. These blocks may represent one or more processors or processing circuitries, operating systems, memories, I/O interfaces, applications, and/or software modules. In other implementations, device 700 may not have all of the components shown and/or may have other elements including other types of elements instead of, or in addition to, those shown herein. While 3D deep planning radiotherapy system 102 is described as performing operations as described in some implementations herein, any suitable component or combination of components of system 102 or similar system, or any suitable processor or processors associated with such a system, may perform the operations described.

A user device can also implement and/or be used with features described herein. Example user devices can be computer devices including some similar components as the device 700, e.g., processor(s) 702, memory 704, and I/O interface 706. An operating system, software and applications suitable for the client device can be provided in memory and used by the processor. The I/O interface for a client device can be connected to network communication devices, as well as to input and output devices, e.g., a microphone for capturing sound, a camera for capturing images or video, audio speaker devices for outputting sound, a display device for outputting images or video, or other output devices. A display device 714, for example, can be connected to (or included in) the device 700 to display images pre- and post-processing as described herein, where such display device can include any suitable display device, e.g., an LCD, LED, or plasma display screen, CRT, television, monitor, touchscreen, 3-D display screen, projector, or other visual display device. Some implementations can provide an audio output device, e.g., voice output or synthesis that speaks text.

One or more methods described herein (e.g., method 200) can be implemented by computer program instructions or code, which can be executed on a computer. For example, the code can be implemented by one or more digital processors (e.g., microprocessors or other processing circuitry), and can be stored on a computer program product including a non-transitory computer readable medium (e.g., storage medium), e.g., a magnetic, optical, electromagnetic, or semiconductor storage medium, including semiconductor or solid state memory, magnetic tape, a removable computer diskette, a random access memory (RAM), a read-only memory (ROM), flash memory, a rigid magnetic disk, an optical disk, a solid-state memory drive, etc. The program instructions can also be contained in, and provided as, an electronic signal, for example in the form of software as a service (SaaS) delivered from a server (e.g., a distributed system and/or a cloud computing system). Alternatively, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (or GPUs) Application Specific Integrated Circuits (ASICs), and the like. One or more methods can be performed as part of or component of an application running on the system, or as an application or software running in conjunction with other applications and operating system.

One or more methods described herein can be run in a standalone program that can be run on any type of computing device, a program run on a web browser, a mobile application ("app") run on a mobile computing device (e.g., cell phone, smart phone, tablet computer, wearable device (wristwatch, armband, jewelry, headwear, goggles, glasses, etc.), laptop computer, etc.). In one example, a client/server architecture can be used, e.g., a mobile computing device (as a client device) sends user input data to a server device and receives from the server the final output data for output (e.g., for display). In another example, all computations can be performed within the mobile app (and/or other apps) on the mobile computing device. In another example, computations can be split between the mobile computing device and one or more server devices.

Although the description has been described with respect to particular implementations thereof, these particular implementations are merely illustrative, and not restrictive. Concepts illustrated in the examples may be applied to other examples and implementations. For example, prostate cancer treatment is described and shown herein as an example to illustrate an implementation of the disclosed subject matter, it will be appreciated that the system and methods described herein can be extended to other cancer sites, such as liver, lung, head, neck, etc. Also, it will be appreciated that the FCNN architecture shown in FIG. 3 is an example for illustration purposes. Other implementations of the FCNN can include a simpler or more complicated structure than the example shown in FIG. 3.

Note that the functional blocks, operations, features, methods, devices, and systems described in the present disclosure may be integrated or divided into different combinations of systems, devices, and functional blocks as would be known to those skilled in the art. Any suitable programming language and programming techniques may be used to implement the routines of particular implementations. Different programming techniques may be employed, e.g., procedural or object-oriented. The routines may execute on a single processing device or multiple processors. Although the steps, operations, or computations may be presented in a specific order, the order may be changed in different particular implementations. In some implementations, multiple steps or operations shown as sequential in this specification may be performed at the same time.

What is claimed is:

1. A computer-implemented method to predict a three-dimensional dose distribution, the method comprising:
    receiving, with one or more processors, input data including a three-dimensional voxel image that includes two-dimensional slices, wherein each voxel in the three-dimensional voxel image includes a distance from the voxel to a closest organ surface in three-dimensional space;
    providing at least a portion of the input data to a deep fully convolutional neural network (FCNN);
    programmatically analyzing in parallel, by the one or more processors, two or more of the two-dimensional slices in the input data;
    outputting, by the deep FCNN, a three-dimensional dose distribution prediction that includes a dose prediction for each of the two or more of the two-dimensional slices, wherein the dose prediction for each of the two or more of the two-dimensional slices is independent of dose predictions for other two-dimensional slices and wherein the dose prediction is based on the distance from corresponding voxels to the closest organ surface;
    providing, by the one or more processors, the three-dimensional dose distribution prediction as output;

generating, by the one or more processors, a treatment plan based on the three-dimensional dose distribution prediction, wherein the treatment plan includes an electronic file that includes instructions to cause a radiotherapy system to treat a body of a patient associated with the three-dimensional voxel image using radiation; and transmitting the treatment plan to the radiotherapy system for treatment of the patient associated with the three-dimensional voxel image, wherein the radiotherapy system applies radiation to the patient based on the treatment plan.

2. The method of claim 1, wherein the distance from the voxel to the closest organ surface in the three-dimensional space is positive if the voxel is within a corresponding organ and wherein the distance is negative if the voxel is outside of the corresponding organ.

3. The method of claim 1, wherein the deep FCNN is trained based on backpropagation that minimizes a loss function between predicted dose maps and corresponding previously used clinical plans.

4. The method of claim 1, wherein the treatment plan includes one or more parameters for radiation treatment that include one or more of an amount of radiation to be applied in terms of units of radiation per unit of volume or mass, a time duration for which radiation is to be applied, a count of times radiation is to be applied, a type of radiation to be applied, or a physical location within an organ of the patient.

5. The method of claim 3, wherein the deep FCNN is further trained by implementing a dropout that reduces overfitting by:
  randomly setting one or more neuron in the deep FCNN to zero such that the neuron does not contribute to the backpropagation; and
  training remaining neurons in the deep FCNN after the one or more neurons are set to zero.

6. The method of claim 1, wherein the three-dimensional dose distribution prediction is in units of Gy representing energy deposited per unit of mass (Joule/kilogram).

7. The method of claim 1, wherein each voxel in the three-dimensional voxel image further includes features channels that describe distances from the voxel to organs of interest that do not receive radiation during application of the radiation to the patient.

8. The method of claim 1, wherein the radiotherapy system is a linear accelerator (LINAC) and the treatment plan includes one or more of a parameter associated with mechanical movement of one or more components in the LINAC.

9. The method of claim 1, wherein the radiotherapy system is a linear accelerator (LINAC) and the electronic file is in a data format accepted by the LINAC.

10. The method of claim 9, wherein the data format includes an extension of a Digital Imaging and Communications in Medicine (DICOM) format including a DICOM-Radiation Therapy (DICOM-RT) data format.

11. The method of claim 10, wherein the electronic file includes one or more DICOM-RT objects, and wherein the one or more DICOM-RT objects include one or more of an RT image, one or more RT structure sets, an RT plan, an RT dose, an RT beams treatment record, an RT brachy treatment record, or an RT treatment summary.

12. A system comprising:
  one or more processors coupled to a computer readable memory having stored thereon software instructions that, when executed by the one or more processors, cause the one or more processors to perform operations including:
    receiving input data including a three-dimensional voxel image that includes two-dimensional slices, wherein each voxel in the three-dimensional voxel image includes a distance from the voxel to a closest organ surface in three-dimensional space;
    programmatically analyzing in parallel two or more of the two-dimensional slices in the input data
    outputting, by a deep fully connected neural network (FCNN), a three-dimensional dose distribution prediction that includes a dose prediction for each of the two or more of the two-dimensional slices, wherein the dose prediction for each of the two or more of the two-dimensional slices is independent of dose predictions for other two-dimensional slices and wherein the dose prediction is based on the distance from corresponding voxels to the closest organ surface;
    providing the three-dimensional dose distribution prediction as output;
    generating a treatment plan based on the three-dimensional dose distribution prediction, wherein the treatment plan includes an electronic file that includes instructions to cause a radiotherapy system to treat a body of a patient associated with the three-dimensional voxel image using radiation; and
    transmitting the treatment plan to the radiotherapy system for treatment of the patient associated with the three-dimensional voxel image, wherein the radiotherapy system applies radiation to the patient based on the treatment plan.

13. The system of claim 12, wherein:
  the distance from the voxel to the closest organ surface in the three-dimensional space is positive if the voxel is within a corresponding organ and wherein the distance is negative if the voxel is outside of the corresponding organ.

14. The system of claim 12, wherein the one or more processors include a graphics processing unit (GPU) with a plurality of processing units.

15. The system of claim 12, wherein the one or more processors include a neural network processor.

16. The system of claim 12, wherein the one or more processors form a portion of an imaging system.

17. The system of claim 12, wherein each voxel in the three-dimensional voxel image further includes features channels that describe distances from the voxel to organs of interest that do not receive radiation during application of the radiation to the patient.

18. A non-transitory computer readable medium having software instruction stored thereon that, when executed by a processor, cause the processor to perform operations including:
  receiving input data including a three-dimensional voxel image that includes two-dimensional slices, wherein each voxel in the three-dimensional voxel image includes a distance from the voxel to a closest organ surface in three-dimensional space;
  providing at least a portion of the input data to a deep fully convolutional neural network (FCNN);
  programmatically analyzing in parallel two or more of the two-dimensional slices in the input data;
  outputting, by the deep FCNN, a three-dimensional dose distribution prediction that includes a dose prediction for each of the two or more of the two-dimensional slices, wherein the dose prediction for each of the two or more of the two-dimensional slices is independent of dose predictions for other two-dimensional slices and wherein the dose prediction is based on the distance from corresponding voxels to the closest organ surface;

providing the three-dimensional dose distribution prediction as output;

generating a treatment plan based on the three-dimensional dose distribution prediction, wherein the treatment plan includes an electronic file that includes instructions to cause a radiotherapy system to treat a body of a patient associated with the three-dimensional voxel image using radiation; and transmitting the treatment plan to the radiotherapy system for treatment of the patient associated with the three-dimensional voxel image, wherein the radiotherapy system applies radiation to the patient based on the treatment plan.

19. The non-transitory computer readable medium of claim 18, wherein:

the distance from the voxel to the closest organ surface in the three-dimensional space is positive if the voxel is within a corresponding organ and wherein the distance is negative if the voxel is outside of the corresponding organ.

20. The non-transitory computer readable medium of claim 18, wherein the deep FCNN is trained based on backpropagation that minimizes a loss function between predicted dose maps and corresponding previously used clinical plans.

* * * * *